US006441029B1

(12) United States Patent
Elson (10) Patent No.: US 6,441,029 B1
(45) Date of Patent: Aug. 27, 2002

(54) METHOD OF SUPPRESSING TUMOR GROWTH WITH COMBINATIONS OF ISOPRENOIDS AND STATINS

(75) Inventor: Charles E. Elson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/587,737

(22) Filed: Jun. 5, 2000

Related U.S. Application Data (62) Division of application No. 09/027,546, filed on Feb. 23, 1998, now Pat. No. 6,133,312.
(60) Provisional application No. 60/039,790, filed on Mar. 4, 1997.

(51) Int. Cl.[7] .............................................. A61K 31/35
(52) U.S. Cl. ....................................... 514/456; 514/460
(58) Field of Search ................................. 514/460, 456

(56) References Cited

U.S. PATENT DOCUMENTS

| | | |
|---|---|---|
| 4,789,554 A | 12/1988 | Scavone et al. |
| RE33,885 E | 4/1992 | Mattson |
| 5,157,132 A | 10/1992 | Tan et al. |
| 5,190,618 A | 3/1993 | Top et al. |
| 5,204,373 A | 4/1993 | Pearce et al. |
| 5,217,992 A | 6/1993 | Wright et al. |
| RE34,617 E | 5/1994 | Jandacek et al. |
| 5,376,361 A | 12/1994 | Perricone |
| 5,391,765 A | 2/1995 | Pearce et al. |
| 5,393,776 A | 2/1995 | Pearce |
| 5,411,969 A | 5/1995 | Pearce et al. |
| 5,475,029 A | 12/1995 | Bradfute et al. |
| 5,500,154 A | 3/1996 | Bacon et al. |
| 5,554,647 A | 9/1996 | Perricone |
| 5,574,063 A | 11/1996 | Perricone |
| 5,591,772 A | 1/1997 | Lane et al. |
| 5,605,930 A | 2/1997 | Samid |

FOREIGN PATENT DOCUMENTS

| | | |
|---|---|---|
| EP | 0 382 075 A2 | 2/1990 |
| WO | WO 93/16690 | 9/1993 |
| WO | WO 93/20183 | 10/1993 |
| WO | WO 93/23034 | 11/1993 |

OTHER PUBLICATIONS

Carroll et al., Nutr., Lipids, Health, Dis., (1995), 117–21 Abstract Only.*

Larsson, Glycobiology (1993), 3(5), 475–9 Abstract Only.*

S.A. Broitman, et al., "Effect of monoterpenes and mevinolin on murine colon tumor CT–26 in vitro and its hepatic 'metastases' in vivo," Dietary Phytochemicals in Cancer Prevention and Treatment, American Institute for Cancer Research, Plenum Press, New, York pp 111–13 (1996).

K.K. Carroll, et al., "In vitro inhibition of proliferation of MDA–MB–45 human breast cancer cells by combinations of tocotrienols and flavonoids," FASEB J. 9:A868, 1995 (Abstract).

G.L. Case, et al., "Induction of geranyl pyrophosphate pyrophosphatase activity by cholesterol–suppressive isoprenoids," Lipids 30(4):357–359, 1995.

C.E. Elson, "Cholesterol–suppressive and anticarcinogenic actions of anutrient, isoprenoid–derived constituents of food," J. Opt. Nut. 1:16–20, 1992.

C.E. Elson, "The impact of palm oil on experimental carcinogenesis," In Vitamin E in Health and Disease, ed. L. Packer and J. Fuchs, Marcel Dekker, Inc., New York, pp. 533–545, 1993.

C.E. Elson, "Dietary fat and cancer: Anamolous responses to dietary palm oil," Perspectives, A Quarterly Report on New Developments in Fats and Oils Nutrition & Health, pp. 1–4, 1993.

C.E. Elson and S.G. Yu, "Coupling the cholesterol– and tumor–suppressive actions of palm oil to the impact of its minor constituents on mevalonate synthesis," Perspectives, A Periodic Report on New Developments in Fats and Oils Nutrition & Health, p. 1, 1994.

C.E. Elson, Dietary fat and cardiovascular disease: Periodic report on new developments in fats and oils nutrition & health, p. 1, 1994.

C.E. Elson and S.G. Yu, "The chemoprevention of cancer by mevalonate–derived constituents of fruits and vegetables," Am. Ins. Nutr. pp. 607–614, 1994.

C.E. Elson, "Suppression of mevalonate pathway activities by dietary isoprenoids: Protective roles in cancer and cardiovascular disease," Am. Ins. Nutr. pp. 1666S–1672S, 1995.

C.E. Elson, et al., "The cholesterol– and tumor–suppressive actions of palm oil isoprenoids," Nutrition, Lipids, Health and Disease, Ong, A.S.H., et al., AOCS Press, Champaign, IL, pp. 109–116, 1995.

C.E. Elson, "Dietary fat and cardiovascular disease: Anomalous responses to palm oil," Malaysian Oil Sci. & Tech. 4:18–22, 1995.

C.E. Elson and A.A. Qureshi, "Coupling the cholesterol– and tumor–suppressive actions of palm oil to the impact of its minor constituents of 3–hydroxy–3–methylglutaryl coenzyme A reductase activity," Prostagland. Leukot. Essen. Fat. Acids 52:205–208, 1995.

C.E. Elson, "Novel lipids and cancer: Isoprenoids and other phytochemicals," Dietary Fats, Lipids, Hormones, and Tumorigenesis; Heber and Kritchevsky, Plenum Press, New York, pp. 71–86, 1996.

(List continued on next page.)

Primary Examiner—Jerome D. Goldberg
(74) Attorney, Agent, or Firm—Quarles & Brady LLP (57) ABSTRACT

A method of inhibiting the growth of tumor cells is disclosed. In one embodiment, this method comprises the step of exposing tumor cells to an effective amount of a composition comprising at least two compounds selected from the group consisting of tocotrienols, statins and ionones.

8 Claims, 4 Drawing Sheets

OTHER PUBLICATIONS

C.E. Elson, et al., "Functional consequences fo the modulation of 3–hydroxy-3–methylglutaryl coenzyme A(1) reductase by isoprenoids," Mar. 28–Apr. 1, 1998 (AACR Abstract).

S.H. Goh, et al., "Inhibition of tumour promotion by various palm–oil tocotrienols," Int. J. Cancer 57:529–531, 1994.

M.N. Gould, et al., "A comparison of tocopherol and tocotrienol of the chemoprevention of chemically induced rat mammary tumors," Am. J. Nutr. 53:1068S–1070S, 1991.

N. Guthrie, et al., "Inhibition of proliferation of MDA–MB–435 human breast cancer cells by individual tocotrienols from palm oil," AACR Proc. 35:629, 1994 (Abstract).

N. Guthrie, et al., "In vitro inhibition of proliferation fo receptor–positive MCF–7 human breast cancer cells by palm oil tocotrienols," FASEB J. 9:A988, 1995 (Abstract).

N. Guthrie, et al., "Effect of palm oil tocotrienols on the proliferation of ras–transformed NIH–3T3 cells an on farnesyl: and geranylgeranyl:protein transferase activity," FASEB J. 10:A559, 1996 (Abstract).

N. Guthrie, et al., "Combined effects of palm oil tocotrienols, flavonoids and tamoxifen on the proliferation of estrogen receptor–positive MCF–7 human breast cancer cells," AACR Proc. 37:280, 1996 (Abstract).

N. Guthrie, et al., "N15: Palm oil tocotrienols and plant flavonoids act synergistically with each other and with tamoxifen inhibiting proliferation and growth of estrogen––negative MDA–MB–435 and—positive MCF–7 human breast cancer cells in culture," Proceedings of the 1996 PORIM International Palm Oil Congress (Nutrition), pp. 90–99, 1996.

L. He, et al., "Isoprenoids suppress the growth of musine B16 malanomas in vitro and in vivo," Biochem. Mol. Roles Nutr. pp. 001–007, 1996.

J.P. Jani, et al., "Metastasis of B16F10 mouse melanoma inhibited by lovastatin, an inhibitor of cholesterol biosynthesis," Invas. Metas. 13:314–324, 1993.

M. Jung, et al., "Synthesis and biological activity of beta–ionone–derived alcohols for cancer chemoprevention," Anticancer Res. 18:189–192, 1998.

K. Komiyama, et al., "Studies on the biological activity of tocotrienols," Chem. Pharm. Bull. 37(5):1369–1371, 1989.

H. Mo, et al., "End products of plant mevalonate pathways induce apoptosis in tumor cells," (Abstract) 1998.

H. Mo, et al., "IC50 values for the suppression of B16 melanoma cell proliferation by monoterpenoids derivatives," Apr. 18–22, 1998 (ExpBiol 98 Abstract).

K. Nesaretnam, et al., "Effect of tocotrienols on the growth of a human breast cancer cell line in culture," Lipids 30(12):1139–1143, 1995.

K. Nesaretnam, et al., "Tocotrienols inhibit the growth of human breast cancer cells irrespective of estrogen receptor status," Lipids 33(5):461–469, 1998.

R.A. Parker, et al., "Tocotrienols regulate cholesterol production in mammalian cells by post–transcriptional suppression of 3–hydroxy-3–methylglutaryl–coenzyme A reductase," J. Biol. Chem. 268(15):11230–11238, 1993.

B.C. Pearce, et al., "Hypocholesterolemic activity of synthetic and natural tocotrienols," J. Med. Chem. 35(20):3595–3606, 1992.

B.C. Pearce, et al., "Inhibitors of cholesterol biosynthesis. 2. Hypocholesterolemic and antioxidant activities of benzopyran and tetrahydronaphthalene analogues of the tocotrienols," J. Med. Chem. 37(4):526–541, 1994.

A.A. Qureshi, et al., "Response to hypercholesterolemic subjects to administration of tocotrienols," Lipids 30(12):171–1177, 1995.

A.A. Qureshi, et al., "The combined therapy of lovastatin and tocotrienols (palmvitee) in hypercholesterolemic human subjects," Proceedings of the 1996 PORIM International Palm Oil Congress (Nutrition), pp. 168–180, 1996.

B. Tan, "Antitumor effects of palm carotenes and tocotrienols in HRS/J hairless female mice," Nut. Res. 12(1):S163–S173, 1992.

A. Thibault, et al., "Phase I study of lovastatin, an inhibitor of the mevalonate pathway, in patients with cancer," Clin. Can. Res. 2:483–491, 1996.

S.G. Yu, et al., "Dietary beta–ionone suppresses hepatic 3–hydroxy-3–methylglutaryl coenzyme A reductase activity," J. Agric. Food Chem. 42(7):1493–1496, 1994.

S.G. Yu, et al., "Efficacy of beta–ionone in the chemoprevention of rat mammary carcinogenesis," J. Agric. Food Chem. 43(8):2144–2147, 1995.

W. Zurinah, et al., "Effect of tocotrienols on hepatocarcinogenesis induced by 2–acetylaminofluorene in rats," Am. J. Clin. Nutr. 53:1076S–1081S, 1991.

* cited by examiner

FIG. 3

METHOD OF SUPPRESSING TUMOR GROWTH WITH COMBINATIONS OF ISOPRENOIDS AND STATINS

CROSS-REFERENCE TO RELATED APPLICATION

This application is a divisional of Ser. No. 09/027,546, filed Feb. 23, 1998, now U.S. Pat. No. 6,133,312 which claims priority from U.S. provisional patent application No. 60/039,790, filed Mar. 4, 1997, which is incorporated by reference as if fully set forth herein.

This invention was made with U.S. government support awarded by the following agencies: NIH Award No.: CA73418; NIH Grant No. R01 CA49416-05; and USDA Hatch No.: 2656. The United States has certain rights to this invention.

STATEMENT REGARDING FEDERALLY SPONSORED RESEARCH OR DEVELOPMENT

Not applicable.

BACKGROUND

Sundry mevalonate-derived constituents (isoprenoids) of fruits, vegetables and cereal grains suppress chemically-initiated carcinogenesis. This action has been attributed to the isoprenoid-mediated induction of detoxifying activities and to the antioxidant activity of some isoprenoids. Neither action explains the potent impact isoprenoids have on the promotion/progression stage of chemically-initiated carcinogenesis and on the growth of chemically established and implanted tumors (reviewed by Elson, 1995; Elson and Yu, 1994). Isoprenoids differ substantially in the impact they have on tumor growth. Isoprenoids suppress, via post-transcriptional actions (Correll, et al., 1994; Parker, et al., 1993; D. M. Peffley and A. K. Gayen, personal communication), 3-hydroxy-3-methylglutaryl coenzyme A (HMG-CoA) reductase activity, the activity deemed to be rate-limiting for the synthesis of cholesterol. The statins are competitive inhibitors of HMG-CoA reductase. Correlations between the late stage tumor-suppressive potency of diverse isoprenoids and their impact on HMG-CoA reductase activity approach unity. The reductase activity of tumors differs from that of liver in being resistant to sterol feedback regulation. The tumor activity however retains high sensitivity to post-transcriptional regulation as triggered by diverse isoprenoids. As a consequence of the isoprenoid-mediated suppression of HMG-CoA reductase activity the pools of mevalonate pathway intermediates become limiting for the post-translational processing of growth-associated proteins (reviewed by Elson, 1995; Elson and Yu, 1994).

One recent review presented a list of structurally diverse isoprenoids with varying capacity to suppress mevalonate synthesis (Elson, 1995).

SUMMARY OF THE INVENTION

In one embodiment, the present invention is a method for inhibiting tumor cell growth. The method comprises treating the cell with a combination of at least two products of the mevalonate pathway selected from the group consisting of statins, ionones and tocotrienols.

In one preferred embodiment, the ionone is selected from the group consisting of β-ionone; 6-10-dimethyl-undec-3,5-ene-2,9-dione; 6,10-dimethyl-9,10-epoxy-undec-3,5-ene-2-one; 9,10-diacetoxy-6,10-dimethyl-undec-3,5-ene-2-one; 6,10-dimethyl-9,10-diol-undec-3,5-ene-2-one and α-ionone. Preferred tocotrienols include d-γ-tocotrienol, 2-desmethyltocotrienol, d-δ-tocotrienol and d-tocotrienol. Preferred statins include lovastatin, pravastatin, simvastatin and fluvastatin.

In another form, the present invention is a pharmaceutical composition for treating or preventing tumors comprising effective amounts of at least two agents selected from the group consisting of tocotrienols, statins and ionones.

It is an object of the present invention to prevent or reduce tumor growth and metastasis.

It is another object of the present invention to increase the duration of survival of a tumor patient following detection of tumor.

It is another object of the present invention to prevent tumor formation.

Other objects, advantages and features of the present invention will become apparent to one of skill in the art after review of the specification, claims and drawings.

DESCRIPTION OF THE DRAWINGS

FIG. 2A illustrates the effects of γ-tocotrienol and β-ionone.

DESCRIPTION OF THE INVENTION

In one embodiment, the present invention is method of inhibiting the growth of tumor cells by exposing tumor cells to a combination of isoprenoids. In one embodiment of the present invention, the combination comprises at least one tocotrienol and at least one ionone. In another embodiment of the present invention, the combination comprises at least one tocotrienol and at least one statin. In a third embodiment of the present invention, the combination comprises at least one statin at least one ionone. We envision that another suitable embodiment of the present invention would be a combination comprising all three products of the mevalonate pathway.

By "tocotrienol," we mean a member of the following group: The vitamin E family consists of a mixture of vitamers, broadly consisting of tocopherols and tocotrienols. The tocotrienols are epimers of the corresponding tocopherols. The list below describes representative tocopherols and tocotrienols.

| | |
|---|---|
| d-α-tocopherol | 2,5,7,8-tetramethyl-2-(4,8,12-trimethyltridecyl)-chroman-6-ol |
| d-α-tocotrienol | 2,5,7,8-tetramethyl-2-(4,8,12-trimethyltrideca-3,7,11-trienyl)-chroman-6-ol |
| d-β-tocopherol | 2,5,8-trimethyl-2-(4,8,12-trimethyltridecyl)-chroman-6-ol |
| d-β-tocotrienol | 2,5,8-trimethyl-2-(4,8,12-trimethyltrideca-3,7,11-trienyl)-chroman-6-ol |
| d-γ-tocopherol | 2,7,8-trimethyl-2-(4,8,12-trimethyltridecyl)-chroman-6-ol |
| d-γ-tocotrienol | 2,7,8-trimethyl-2-(4,8,12-trimethyltrideca-3,7,11-trienyl)-chroman-6-ol |
| d-δ-tocopherol | 2,8-dimethyl-2-(4,8,12-trimethyltridecyl)-chroman-6-ol |
| d-δ-tocotrienol | 2,8-dimethyl-2-(4,8,12-trimethyltrideca-3,7,11-trienyl)-chroman-6-ol |

-continued

| | |
|---|---|
| d-tocopherol | 2-methyl-2-(4,8,12-trimethyltridecyl)-chroman-6-ol |
| d-tocotrienol | 2-methyl-2-(4,8,12-trimethyltrideca-3,7,11-trienyl)-chroman-6-ol |
| 2-desmethyl-tocotrienol | 2-(4,8,12-trimethyltrideca-3,7,11-trienyl)-chroman-6-ol |

Preferred tocotrienols include d-γ-tocotrienol and 2-desmethyltocotrienol. Other preferred tocotrienols include d-β-tocotrienol, d-δ-tocotrienol and d-tocotrienol.

By "ionone," we mean a member of the following group: Ionones are carotenoid-related compounds widely distributed in nature. α-Ionone and β-ionone and a number of oxygenated derivatives are widely present in plants in free and conjugated forms. Biological activities appear to be restricted to roles as phytoalexins. Ionones are also formed by thermal and photochemical mediated oxidation of carotenes.

Preferred ionones include β-ionone (4-2,6,6-trimethyl-1-cyclohexen-1-yl)-3-buten-2-one; 6-10-dimethyl-undec-3,5-ene-2,9-dione; 6,10-dimethyl-9,10-epoxy-undec-3,5-ene-2-one; 9,10-diacetoxy-6,10-dimethyl-undec-3,5-ene-2-one; and 6,10-dimethyl-9,10-diol-undec-3,5-ene-2-one. Other preferred ionones include α-ionone (4-(2,6,6-trimethyl-2-cyclohexen-1-yl)-3-buten-2-one.

By "statin," we mean a member of the following group: The statins are derivatives of fungi metabolites (ML-236B/compactin/monocalin K) isolated from *Pythium ultimum, Monacus ruber, Penicillium citrinum, Penicillium brevicompactum* and *Aspergillus terreus*. These analogs of 3-hydroxy-3-methylglutaric acid (HMG), compete with HMG-CoA for the substrate binding site on HMG-CoA reductase. Statins are available by prescription in the U.S. For example, lovastatin (Mevacor/Merck), simvastatin (Zocor/Merck), pravastatin (Pravachol/Bristol-Myers Squibb) and fluvastatin (Lescol/Sandoz). There are several more under clinical investigation, including one in late-stage trials at Warner-Lambert. The more lipophilic statins have been associated with some skeletal muscle complaints (myositis, rhabdomyolysis), but most of the side-effects reported in clinical trials have been mild and tolerable (headache, abdominal pain, constipation, flatulence and diarrhea). (Pedersen, T. R., *N. Enql. J. Med.* 333:1350–1351, 1995; Kobashigawa, J. A., et al., *N. Enql. J. Med.* 333:621–627, 1995.) The following list discloses some preferred statins.

| | Trade name | Dosage range (mg/d) | Normal dose (mg/d) |
|---|---|---|---|
| Fungal derivatives | | | |
| lovastatin | Mevacor | 10–80 | 20–40 |
| pravastatin | Pravachol | 10–40 | 20–40 |
| simvastatin | Zocor | 5 . 40 | 5–10 |
| Synthetic compound | | | |
| fluvastatin | Lescol | 20–80 | 20–40 |

The following list describes the chemical formula of preferred statins.

lovastatin: [1S[1a(R),3α,7β,8β(2S,4S),8aβ]]-1,2,3,7,8,8a-hexahydro-3,7-dimethyl-8-[2-(tetrahydro-4-hydroxy-6-oxo-2H-pyran-2-yl)ethyl]-1-maphthalenyl-2-methylbutanoate pravastatin sodium: 1-Naphthalene-heptanoic acid, 1,2,6,7,8a-hexahydro-β,δ,6-trihydroxy-2-methyl-8-(2-methyl-1-oxybutoxy)-1-, monosodium salt [1S-[1α(βs,δS),2α,6α,8β(R),8aα simvastatin: butanoic acid, 2,2-dimethyl-, 1,2,3,7,8,8a-hexahydro-3,7-dimethyl-8-[2 tetrahydro-4-hydroxy-6-oxo-2H-pyran-2-yl)ethyl]-1-napthalenyl ester[1S-[1α,3α,7β,8β,(2S,4S),-8aβ sodium fluvastatin: [R,S-(E)]-(±)-7-[3(4-fluorophenyl)-1-(1-methylethyl)-1H-indol-2-yl]-3,5-dihydroxy-6-heptenoic acid, monosodium salt Preferred statins include lovastatin, pravastatin, simvastatin and fluvastatin.

The Examples below demonstrate a synergistic effect when B16 melanoma cells are treated with combinations of tocotrienols, lovastatin and ionone.

In one Example below, a 68% reduction in B16 melanoma cell number (measured after 48 hours) was obtained. This represented a synergistic effect of 9% over the additive sums of the individual effects. In in vivo tests measuring post-implant survival of melanoma-bearing mice, the P-values for the three comparisons of isoprenoid versus blend treatments fall into the range of 0.66–0.16 whereas the P-values for the three comparisons of isoprenoid versus isoprenoid treatments are greater than 0.88. We first note that all treatments significantly increased the duration of survival ($P<0.03$). Differences between single treatment effects were not significant. The nonparametric test P values fell between 0.64 and 0.95. When we tested the significance of differences between single treatment and blend effects the nonparametric P values fell between 0.16 and 0.64. The trend towards lower P values suggests a possible synergy.

By "synergistic," we mean a percentage reduction in cell number of at least an additional 5% over the additive sum of individual effects or an increase in host survivability of 5% over the additive sum of individual effects.

To reach the present invention, we evaluated the tumor-suppressive potency of a number of diverse isoprenoid compounds in vitro and the potency of two, d-γ-tocotrienol and β-ionone, in vivo. We build on findings that isoprenoids bearing little commonality other than that of sharing a common precursor, isopentenyl pyrophosphate, suppressed melanoma cell proliferation and demonstrate that the effects of individual isoprenoids tested in binary mixtures are additive. We further report that a dietary-relevant intake of d-γ-tocotrienol suppressed the growth of implanted tumors.

Figure 3:
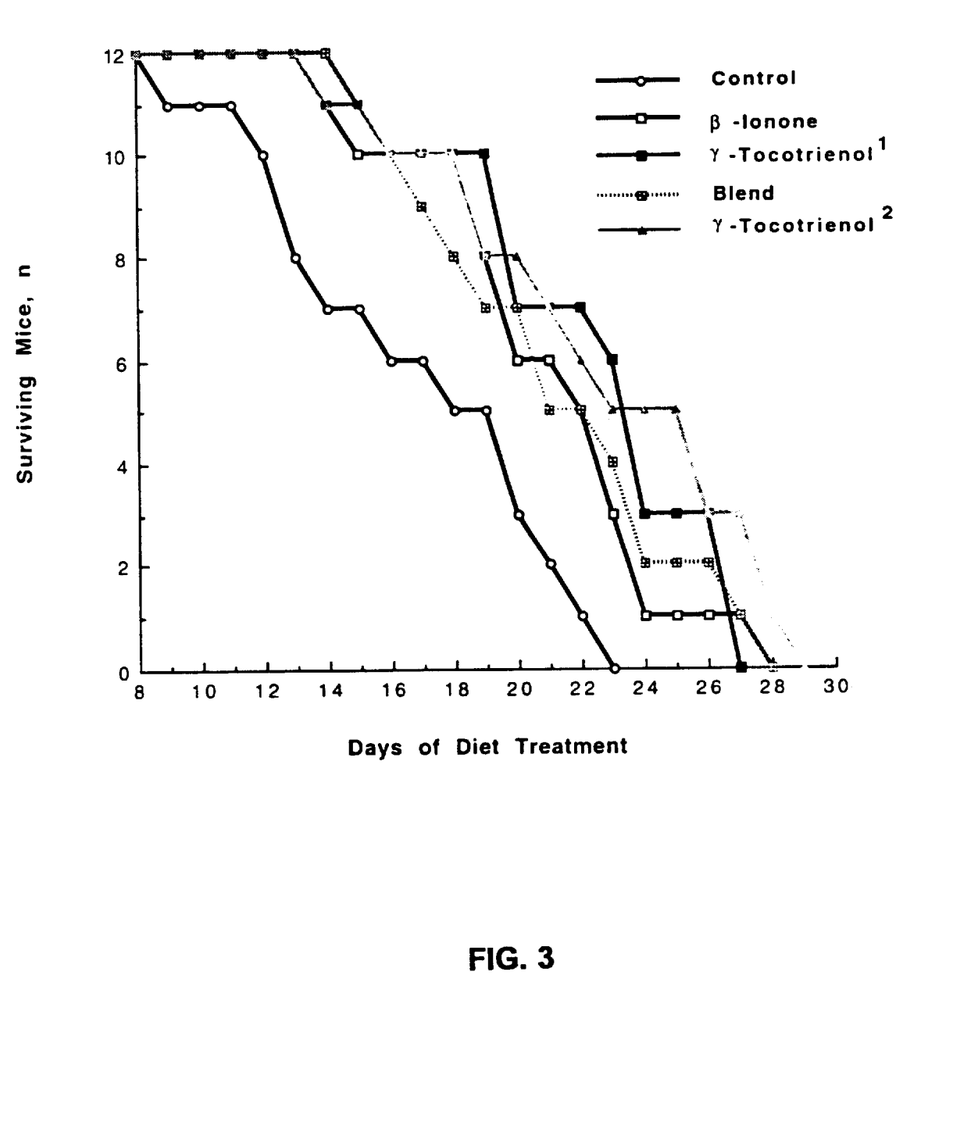
FIG. 3 is a survival curve for host mice receiving isoprenoid-enriched diets following the detection of a solid implanted B16 melanoma.

The study described below in the Examples estimated the concentrations of structurally diverse isoprenoids required to inhibit the increase in a population of murine B 16(F10) melanoma cells during a 48 hour incubation by 50% ($IC_{50}$ value). The $IC_{50}$ values for d-limonene and perillyl alcohol, the monoterpenes in Phase I trials, were respectively 450 and 250 µmol/L; related cyclic monoterpenes (perillaldehyde, carvacrol, thymol), an acyclic monoterpene (geraniol) and the end ring analog of β-carotene (β-ionone) had $IC_{50}$ values in the range of 120–150 µmol/L. The $IC_{50}$ value estimated for farnesol, the side chain analog of the tocotrienols (50 µmol/L) fell midway between that of α-tocotrienol (110 µmol/L) and those estimated γ-(20 µmol/L) and δ-tocotrienol (10 µmol/L). A novel tocotrienol lacking methyl groups on the tocol ring proved to be extremely potent ($IC_{50}$, 0.9 µmol/L). In the first of two diet studies, experimental diets were fed to weanling C57BL female mice for 10 days prior to and for 28 days following the implantation of the aggressively growing and highly metastatic B16(F10) melanoma. The isomolar (116 μmol/kg diet) and the Vitamin E-equivalent (928 μmol/kg diet) substitution of d-γ-tocotrienol for dl-α-tocopherol in the AIN-76A diet produced 36% and 50% retardations respectively in tumor growth ($P<0.05$). In the second study, melanomas were established before mice were fed experimental diets formulated with 2 mmol/kg d-γ-tocotrienol, β-ionone individually and in combination. A fourth diet was formulated with 4 mmol/kg d-γ-totrienol (FIG. 3). Each treatment increased ($P<0.03$) the duration of host survival. The present invention stems from our finding that the effects of some individual isoprenoids were additive and the effects of other individual isoprenoids are synergistic. This finding suggests that particular combination of isoprenoids would be uniquely suitable for chemotherapeutic applications.

The methods of the present invention may be realized in several embodiments. In one embodiment, the human or animal subject is administered the isoprenoid combination in a pharmaceutical or veterinary composition containing a safe and effective dose. In another embodiment, the subject is fed a food that has been enriched with the isoprenoid combination. Statins are now available only by prescription and would not preferably be added to food.

The human and animal foodstuffs and pharmaceutical preparations for use in the methods of the present invention are those containing the selected isoprenoid combination additionally combined with conventional animal feeds, human food supplements or approved pharmaceutical diluents and excipients.

Highly active tocotrienols include d-γ-tocotrienol, d-δ-tocotrienol and 2-desmethyltocotrienol, both of which occur naturally. d-γ-tocotrienol and d-δ-tocotrienol may be extracted from tocotrienol-rich fractions of rice brand oil or of palm oil by published methods. 2-desmethyltocotrienol may be extracted from tocotrienol-rich fractions of rice bran oil by published methods.

β-Ionone may be obtained from a variety of commercial sources. For example, β-ionone can be found at catalog no. W25950-0, Aldrich Flavors and Fragrances; β-ionone is also listed in Aldrich Fine Chemical and Sigma catalogs. Other ionones are listed in the above catalogs and in Bedoukian Research Distinctive Perfume & Flavor Ingredients.

Lovastatin may most easily be obtained commercially.

The isoprenoid combination, in addition to being added to the subject's food, can be administered in the form of pharmaceutical or veterinary compositions such as enteric coated tablets, capsules, powders, solutions or emulsions. The precise amount to be administered will depend upon the isoprenoids employed, the route of administration, the weight of the subject and the nature of the condition. We note that the melanoma cell line used for the Examples below is known to be extremely resistant to chemotherapeutic measures. Therefore, the actual dosage used in patient treatment may be less than that proposed from our experimental model.

Generally, the quantities of the agents required in a pharmaceutical combination will provide a daily intake substantially less than the quantities required when the agents are administered individually. Perillyl alcohol, an isoprenoid in clinical evaluation for efficacy as antitumor agents tumor therapy, is adminstered at levels in excess of 8 g/day; lovastatin is clinically effective, but poorly tolerated, for treating brain tumors at doses ~2 g/d (>20× the dose administered for hypercholesterolemia). The tocotrienols effectively lower cholesterol levels when consumed at dose levels of <300 mg/day. Due to the synergistic actions of the agents, we anticipate a preferable blend will contain 250 mg tocotrienol/2000 mg ionone/150 mg statin (~2 mg/kg body wt.) per day. A maximal preferred dosage would contain 500 mg tocotrienol/4000 mg ionone/300 mg statin per day.

A representative pharmaceutical enteric coated tablet has the formula:

Active principles:

| | |
|---|---|
| d-γ-tocotrienol | 50 mg |
| 6,10-dimethyl-9,0-epoxy-undec-3,5-ene-2-one | 400 mg |
| statin | 30 mg |

Excipients/fillers
Microcrystalline cellulose
Sodium starch glycolate
Corn starch
Hydrogenated vegetable oil wax
Magnesium stearate
Talc The preferred normal per diem dosage is 5 tablets.

A bar or cookie may be of any desired type which is prepared first and afterwards dosed with a small amount of liquid containing the active principles:

| | |
|---|---|
| d-γ-tocotrienol | 50 mg |
| 6,10-dimethyl-9,0-epoxy-undec-3,5-ene-2-one | 400 mg |

It is preferable that suitable flavorings are present in the bar or cookie to impart an acceptable level of palatability. It is essential that the active principles are added after any baking or heating process has occurred and cooling is complete since the tocotrienols are heat labile. Such a bar or cookie may advantageously be packed in a hermetically sealed packet.

Because the tocotrienols and ionones are relatively non-toxic, doses larger than the higher figure stated above may be administered if desired, particularly with the enteric coated composition. Higher doses may, however, markedly reduce gut flora and lead to gastrointestinal disturbances. It is recommended that when the compositions of the instant invention are administered, the daily intake of vitamin E is restricted. The more lipophilic (fat loving) statins have been associated with some skeletal muscle complaints (myositis, rhabdomyolysis), but most of the side effects reported in clinical trials have been mild and tolerable (headache, abdominal pain, constipation, flatulence and diarrhea. Patients (Thibault, et al., *Clinical Cancer Research* 2:483–491, 1996) tolerated intakes approaching 2 g/d (25 mg/kg body wt).

It will be apparent to those skilled in the art that numerous modifications or changes may be made without departing from the spirit or the scope of the present invention. Thus, the invention is only limited by the following claims.

EXAMPLES

Abbreviations used: HMG CoA, 3-hydroxy-3-methylglutaryl coenzyme A; $IC_{50}$, the concentration required to suppress the increase in the population of melanoma cells by 50%; TRF, tocotrienol-rich fraction of palm oil; $TRF_{25}$, oryzanol-free tocotrienol-rich fraction of rice bran oil.

A. Materials and Methods

Isoprenoids: d-Limonene (97%), perillyl alcohol (99%), perillaldehyde (92%), carvacrol (98%), thymol (98%), β-ionone (96%), geraniol (98%), farnesol (96%) and dl-α-tocopherol (97%) were purchased from Aldrich Chemical, Milwaukee, Wis. An abridged list of concentrated natural sources and aroma characteristics of these isoprenoids appears below in Table 1. A preliminary study revealed the very potent tumor-suppressive action of the oryzanol-free tocotrienol-rich fraction of rice bran oil ($TRF_{25}$) prepared by molecular distillation (Dr. Laxman Singh, Vitamins, Inc., Chicago, Ill.). The fraction consisted of 6% d-α-tocopherol, 12.5% d-α-tocotrienol, 21% d-γ-tocotrienol, 10% d-δ-tocotrienol, 4.5% d-tocotrienol, 17% d-2-desmethyl tocotrienol, 18% unidentified tocotrienol isomers and 10% sterols and triglycerides (Qureshi, et al., unpublished data). The major constituents, d-α-tocotrienol, d-γ-tocotrienol, d-δ-tocotrienol, and d-2-desmethyl tocotrienol, were isolated by Advanced Medical Research, Madison, Wis. A chromatographic procedure was developed to separate d-γ-tocotrienol from the tocotrienol-rich fraction (TRF) of palm oil (36% d-γ-tocotrienol, 18% d-α-tocotrienol, 12% d-δ-tocotrienol and 22% d-α-tocopherol), a gift of the Palm Oil Research Institute of Malaysia, Kuala Lumpur, Malaysia. Silica gel (Merck, 60μ, 150 g) suspended in hexane was poured into a 350 mL glass funnel with a fritted disc. The gel was washed with one L hexane prior to being loaded with 5 g of the TRF in 20 mL hexane. The tocols were eluted with the sequential applications of 500 mL mixtures of diethyl ether (5%, 10%, 12%, 14%, 16%, 18%, 20%, 22%, 25% and 30%) in hexane. The elution of each application of solvent into a filter flask was speeded by the application of vacuum produced by water aspiration. The eluates were taken to dryness under vacuum, the residues redissolved in hexane and identified according to retention time and absorption profile using an analytical HPLC system. The fraction eluted with 18% diethyl ether was predominantly (98%) d-γ-tocotrienol.

$IC_{50}$, Determinations: Murine B16(F10) melanoma cells, a tumor cell line with high metastatic potential (Tsukamoto, et al., 1991) obtained from Dr. William B. Ershler, were grown in monolayer culture (35×10 mm flasks) in 3 mL RMPl 1640 media (Sigma) supplemented with 10% newborn calf serum (GIBCOBRL, Grand Island, N.Y.) and 80 mg/L gentamycin (Sigma, St. Louis, Mo.). Cultures, seeded with $1-1.5 \times 10^5$ cells, were incubated for 24 hours at 37° C. in a humidified atmosphere of 5% $CO_2$. Isoprenoids, dissolved in absolute ethanol, were added at 24 hours (0 time); all cultures contained 5 mL ethanol/L (85 μmol/L). The cultures were incubated for an additional 48 hours. The media was removed and the monolayers were washed twice with Hanks' Balanced Salt Solution (Sigma) and then incubated with a trypsin-EDTA solution (Sigma) at 37° C. for 2 minutes. Trypsin was inactivated by suspending the cells in medium containing 10% fetal bovine serum (Sigma). The cells were pelleted at 250×g and resuspended in Hanks' Balanced Salt Solution. Viable cells, cells that excluded 0.4% trypan blue (GIPCOBRL), were counted with a hemocytometer; 24 hour cell counts were deducted from final cell counts to provide an estimate of the net increase in cell number. The calculation of the concentration of an isoprenoid required to inhibit the net increase in the 48 hour cell count by 50% ($IC_{50}$) is based on plots of data from three or more evaluations.

Animal Studies: This evaluation of the tumor-suppressive potency of diverse isoprenoids was extended with two dietary studies. The first examined the impact of a diet-relevant intake of d-γ-tocotrienol on the growth of B16(F10) melanomas in host mice. The second study evaluated the impact of pharmacological intakes of d-γ-tocotrienol and β-ionone on the post-implant survival of melanoma-bearing mice. We first prepared a basal diet mix, patterned after the AIN-76A formulation (American Institute of Nutrition, 1977) but free of corn oil and dl-α-tocopherol. These ingredients and Vitamin E-stripped corn oil were purchased from Teklad Test Diets, Madison, Wis. Stock solutions of dl-α-tocopherol (80 μmol/g) and d-γ-tocotrienol (80 μmol/g) were prepared with vitamin E-stripped corn oil. Stock solutions of the tocols, diluted with vitamin E-stripped corn oil, were mixed with the basal diet to provide finished diets containing 5% corn oil and specified tocol concentrations. Where noted, β-ionone was added to the oil. The diets, mixed weekly, were stored under refrigeration. Food cups were cleaned and refilled daily.

Experiment 1: Weanling C57BL female mice (Harlan-Sprague Dawley, Madison, Wis.) were housed in groups of four on wood shavings in plastic cages and maintained at 25° C. with a 12 hour light-dark cycle. The four groups of mice (20/group) were fed experimental diets for 10 days prior to and for 28 days following the implantation of B16 melanoma cells. The split plot design consisted of four treatments comprised of two tocols, dl-α-tocopherol and d-γ-tocotrienol, each presented at two levels, 116 and 924 μmol/kg diet. This design permitted two comparisons of diets equal in tocol content and one comparison of diets about equal in d-α-tocopherol equivalents. Lacking a definitive estimate of the biological activity of d-γ-tocotrienol, we considered reports that the 2, 5, 8 (d-β-) and 2, 7, 8 (d-γ-) trimethyl tocopherols have similar oxygen scavenging activity (maximally 66% that of the 2, 5, 7, 8 (d-α-) tetramethyl tocopherol) and as a class, the tocotrienols have 5–30% of the biological activity of the tocopherols (Karnal-Eldin and Appelqvist, 1996) in developing the rough estimate that d-α-tocopherol has, minimally, 6-fold the biological activity of d-γ-tocotrienol. We then corrected for the biological activity of the dl-α-tocopherol mixture (70% of the activity of d-α-tocopherol) in arriving at the 8:1 tocotrienol/tocopherol ratio used in formulating the experimental diets. Melanoma cells, cultured and harvested as previously, described (Shoff, et al., 1991), were washed twice with RPMI 1640 containing 10% Fetal Bovine Sera (GIBCOBRL). The pelleted cells were suspended in RPMI 1640 and counted (98% viable) after a 1:20 dilution in 0.4% trypan blue. The cells were further diluted in RPMI 1640 ($1 \times 10^8$ cells/L) and 0.1 mL of the suspension ($1 \times 10^4$ cells) was injected subcutaneously into the flank of each mouse. The study was terminated day 28 when the first mouse, a mouse in the control group, died. The mice were killed by $CO_2$ overdose and the tumors were excised and weighed. The protocol was reviewed and approved by College of Agricultural and Life Sciences Animal Care Committee.

Experiment 2: Weanling female C57BL female mice (n=60, Harlan Sprague-Dawley) were acclimated to the housing conditions and AIN-76A diet (116 μmol dl-α-tocopherol/kg diet) as described above. Tumors were implanted and the mice continued to receive the AIN-76A diet. Beginning on day 8 post-implant the mice were palpated daily for the presence of a tumor. Tumors were first detected on day 14. Random numbers were generated for assigning each mouse in a sequential subset of five to a diet. Experimental treatments provided 2 and 4 mmol d-γ-tocotrienol/kg diet. We additionally tested the impact of β-ionone (2 mmol β-ionone/kg AIN-76A diet) and that of a blend of the two isoprenoids (2 mmol each/kg diet) on the survival of the mice. The mice were continued on the respective experimental diets; moribund mice, identified by the Research Animal Resource-trained supervisor blinded to the experimental design, were killed by $CO_2$ overdose and the tumors were excised and weighed. The protocol was reviewed and approved by College of Agricultural and Life Sciences Animal Care Committee.

Statistical Methods: StatView and SuperANOVA software (Abacus Concepts, Berkeley, Calif.) were used for the assessment of treatment-mediated effects. Treatment-mediated differences in body and tumor weights, days to tumor appearance and days to morbidity were identified with split plot analysis of variance and pairwise t-tests of least squares means. Treatment-mediated differences in days to morbidity were also assessed using parametric (paired t-test) and nonparametric (Wilcoxon signed rank) tests (Haycock, et al., 1992).

B. Results

Figure 1:
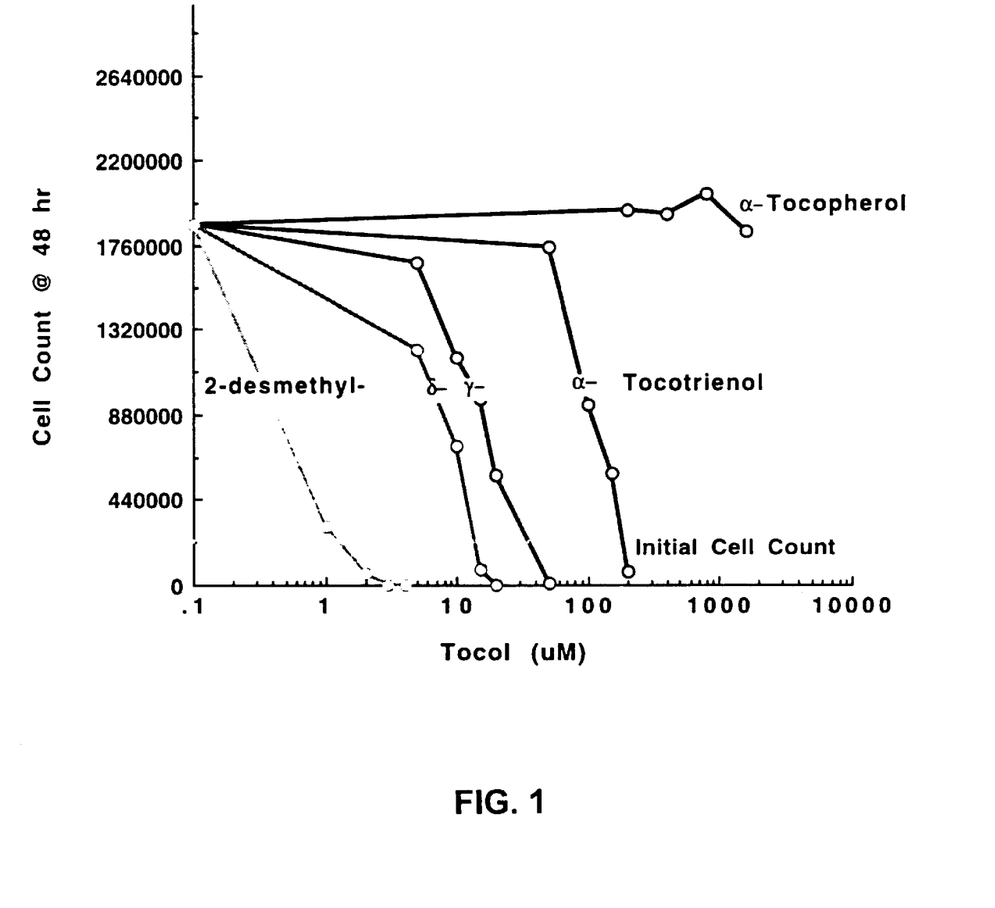
FIG. 1 graphs the dose-dependent impact of tocols on the proliferation of melanoma B16 cells.

FIG. 1 is a representative evaluation of the dose-dependent impact of five different tocols on the proliferation of melanoma B16 cells. Cultures (3 mL) seeded with 1–1.5× $10^5$ cells were incubated for 24 hours prior to the introduction of the tocols. Viable cells were counted at 48 hours following the addition of the tocols. The cell count at 24 hours (0 time) is shown by the dashed line. The intersection of the solid horizontal line and the line plotted for each tocol indicates the concentration at which the tocol suppressed by 50% the increase in cell number during the incubation ($IC_{50}$ value). $IC_{50}$ values (mean, SD and n) for all isoprenoids tested are listed on Table 1. Referring to FIG. 1, dl-α-Tocopherol had no impact on cell number. The growth-suppressive potency of the individual tocotrienols was inverse to the number of methyl groups on the 6-chromanol ring: d-α-tocotrienol (methyl groups at carbons 5, 7, 8 and 2)<<d-γ-tocotrienol (methyl groups at carbons 7, 8 and 2)<d-δ-tocotrienol (methyl groups at carbons 8 and 2)<<d-2-desmethyl tocotrienol (no methyl groups) (Table 1).

Within this series of tocotrienols the $IC_{50}$ value was inversely related to the number of methyl groups on the 6-chromanol ring. Similarly, the $IC_{50}$ values calculated from plots for the more polar monoterpenoid alcohols, perillyl alcohol ([R]4-isopropenyl-1-methanol-cyclohexene), perillaldehyde ([R]-4-isopropenyl-1-carboxaldehyde cyclohexene), thymol (5-methyl-2-isopropylphenol), carvacrol (5-isopropyl-2-methylphenol) and geraniol (trans 3,7-dimethyl-2,6-octadien-1-ol) were much lower than that for d-limonene ([R]4-isopropenyl-1-methyl-1-cyclohexene). The $IC_{50}$ value for β-ionone, the end ring analog of β-carotene, matched those of the more polar monoterpenes (Table 1). The $IC_{50}$ for farnesol (trans, trans 3,7,11-trimethyl-2,6,10 dodecatrien-1-ol), a sesquiterpene and a structural analog to the side chain of the tocotrienols, fell midway between those of d-α-tocotrienol and d-γ- and d-δ-tocotrienol.

The first dietary study evaluated the impact of d-γ-tocotrienol and dl-α-tocopherol on days to detection of a solid tumor and growth of implanted B16 melanomas. As noted above the design permitted two comparisons of treatments providing equal tocol concentration (116 and 928 μmol/kg diet) and one comparison of treatments providing about 80 mol d-α-tocopherol equivalents (35 mg)/kg diet. At the time of tumor implant the body weight of mice receiving the high tocopherol diet was significantly lower than that of mice receiving the low tocol diets (Table 2). At 28 days post-implant the melanomas accounted for 15% of the weight of mice receiving the AIN-76A diet. Two tocols were tested, each at two levels. The split plot analysis of variance showed the effects of tocols (P<0.001) and levels (P<0.04) on 28 day tumor weight were significant; there was no evidence of an interaction between the two factors (P<0.77). Least mean squares analyses confirmed the tumor growth-suppressive action of γ-tocotrienol (Table 2). The other measure of tumor growth, days post-implant to tumor detection showed tocol (P<0.03), level (P<0.01) and the interaction (P<0.02) to be significant. The least mean squares analysis showed that the effect of the treatment providing 928 μmol d-γ-tocotrienol/kg diet on this measure of tumor growth differed significantly from the effects of the other treatments.

Figure 2A:
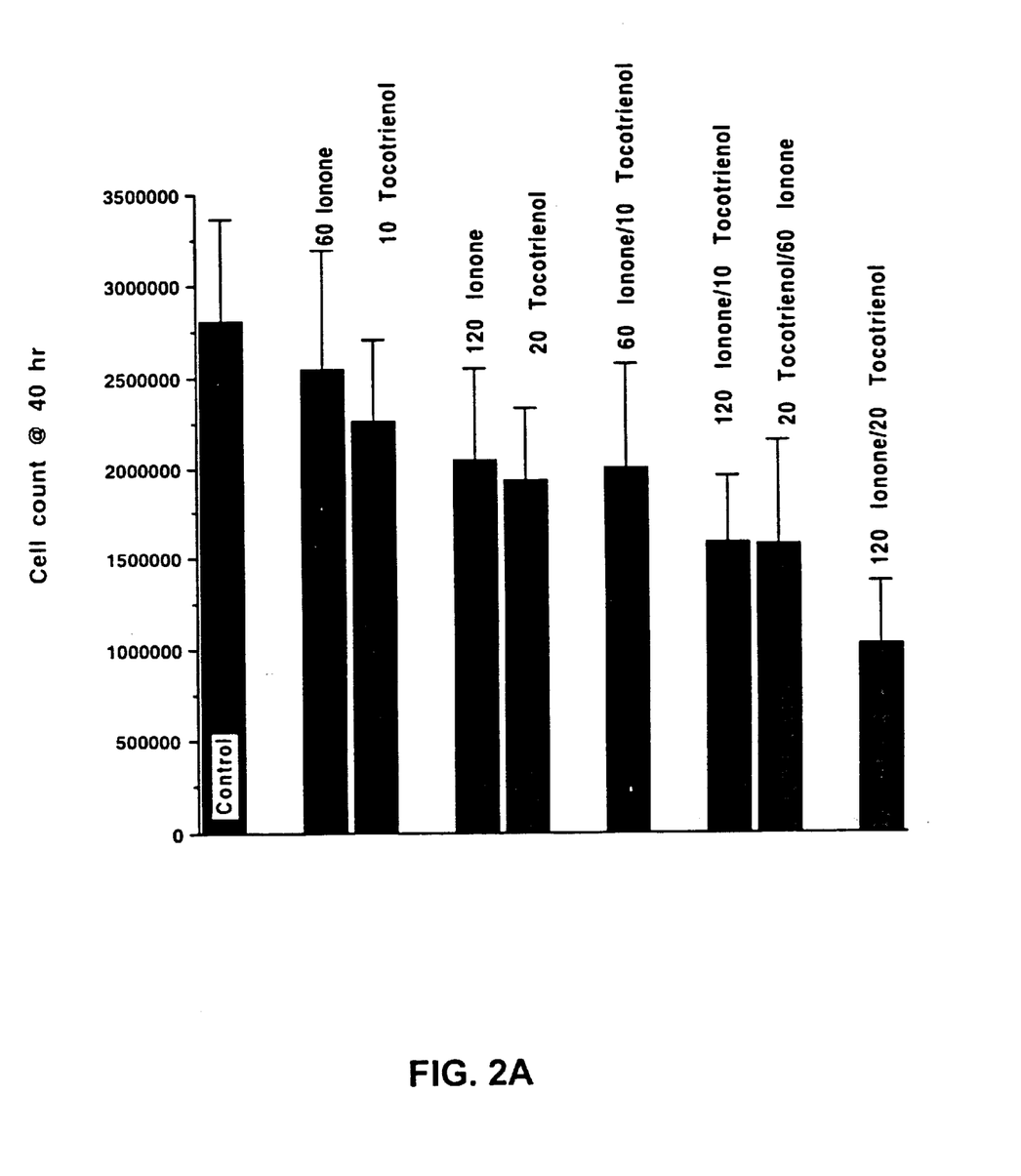
FIG. 2A and B illustrate the effects of combinations of γ-tocotrienol, β-ionone and carvacrol on B16 melanoma cell populations.

We next determined that the effects of the isoprenoids on the growth of B16 melanoma cells in culture are additive, and in some cases, synergistic. FIG. 2A illustrates the additive effects of γ-tocotrienol and β-ionone on B16 melanoma cell populations. Values are means±SD, n=28; pooled SEM=36 (×$10^4$). Cell counts calculated to show the decreased population relative to the control are listed on the insert table.

Figure 2B:
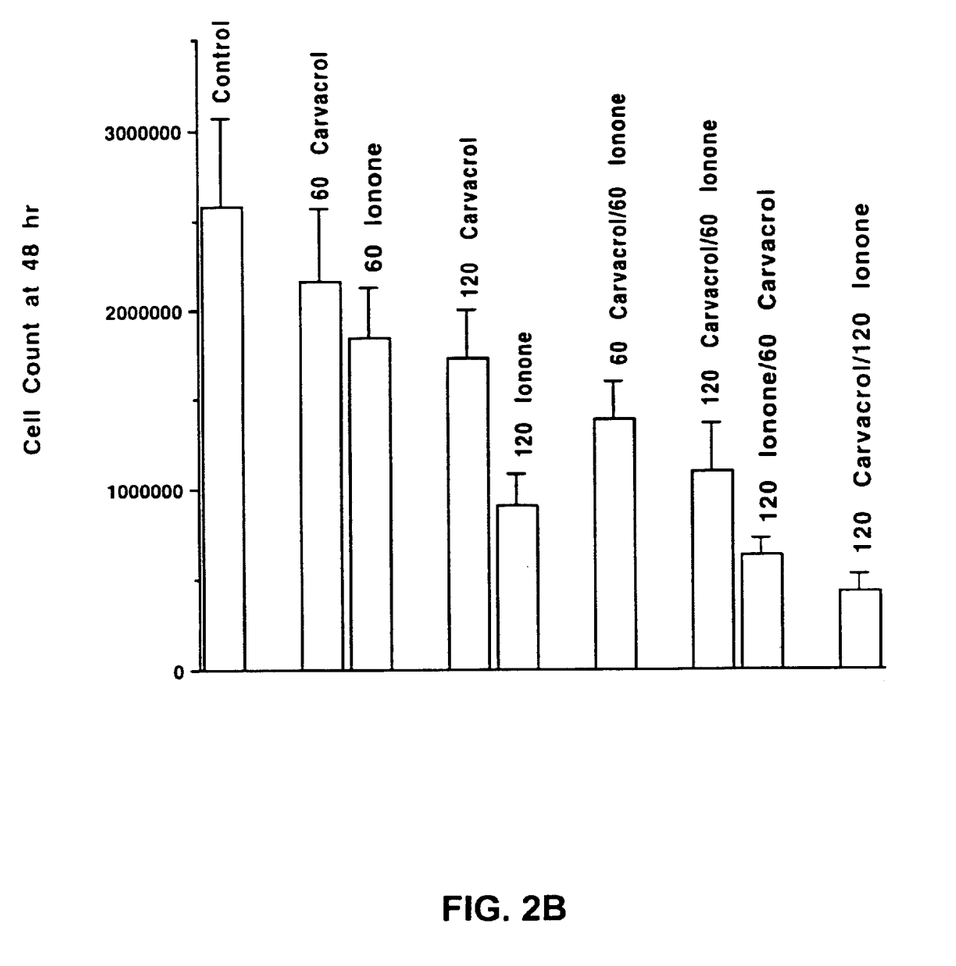
FIG. 2B illustrates the effects of carvacrol and β-ionone.

FIG. 2B illustrates the additive effects of carvacrol and β-ionone on B16 melanoma cell populations. Values are means±SD, n=28; pooled SEM=62 (×$10^4$). Cell counts calculated to show the decreased population relative to the control are listed in the inset table. [a-h]Means not sharing a superscript (a>b>c>d>e>f>g>h) are different (P<0.001). Referring to FIG. 2, B16 melanoma cells were incubated with β-ionone and d-γ-tocotrienol in one test (FIG. 2A). d-γ-Tocotrienol (7.5 μmol/L) and β-ionone (50 μmol/L) reduced the 48 hour cell count by 19% and 10% respectively (FIG. 2A). The 34% reduction in cell number achieved with the paired isoprenoids exceeded the 29% reduction predicted by the sum of the individual effects (FIG. 2A, inset). At higher concentrations d-γ-tocotrienol (15 μmol/L) and β-ionone (100 μmol/L) reduced the 48 hour cell count by 34% and 16% respectively; the additive effect, a 68% reduction in cell number, was also greater than the sum of the individual effects (59%) (FIG. 2A, inset).

Whereas the foregoing results pointed to a synergistic action of d-γ-tocotrienol and β-ionone, the study pairing carvacrol and β-ionone revealed only an additive effect (FIG. 2B). Carvacrol (50 μmol/L) and β-ionone (75 μmol/L) reduced the 48 hour cell count by 25% and 31% respectively; the additive effect, a 48% reduction in cell number, was less than the 56% reduction predicted by the sum of the individual effects. Carvacrol (100 μmol/L) and β-ionone (150 μmol/L) reduced the cell count by 35% and 65% respectively; the additive effect, an 84% reduction in cell number, again was less than the 100% reduction predicted by the sum the individual effects (FIG. 2B, inset). The reduction in cell number predicted by the sum of the individual effects of the isoprenoids was highly correlated with that achieved with the paired isoprenoids (r=0.91, n=8, P<0.01).

We then asked if either dietary d-γ-tocotrienol or β-ionone would prolong the survival of mice bearing implanted melanomas. Dietary treatments were initiated following the detection of solid tumors. We also asked whether these structurally diverse isoprenoids would have an additive effect on survival. The experimental groups were constructed by random assignment of each member of successive subsets of 5 mice to one of the experimental diets. Time to tumor detection did not vary between groups (Table 3). Treatments increased median duration of survival by 42±4.5% and the mean duration of survival by 30% (P<0.005); differences between duration of survival means of the experimental groups were not significant (Table 3, FIG. 3). FIG. 3 is a survival curve for host mice receiving isoprenoid-enriched diets following the detection of a solid implanted B16 melanoma. Mean survival durations are presented on Table 4. β-ionone and γ-tocotrienol[1] treatments provided 2 mmol of the isoprenoid/kg diet; the blend provided 2 mmol of each isoprenoid/kg diet; and γ-tocotrienol[2] provided 4 mmol γ-tocotrienol/kg diet.

According to the experimental design, each animal within a subset of 5 could be paired with another member of the subset for testing. P-values for the pairwise comparisons, assuming normal and anormal distributions, are listed on Table 4. All analyses revealed highly significant differences between the control and treatment group means; differences between the treatment group means were not significant. Lending additional creditability to the results of the in vitro analysis showing an at least additive effect of the two isoprenoids is the trend shown on Table 4. Whereas the P-values for the three comparisons of isoprenoid versus isoprenoid treatments are greater than 0.88, the P-values for the three comparisons of isoprenoid versus blend treatments fall in the range 0.66–0.16.

C. Discussion

The B16(F10) melanoma provides a rigorous model for assessing, in vitro and in vivo, the potency of pharmacological agents (Gruber, et al., 1992; Kuwashima, et al., 1990; Mac Neil, et al., 1992; Tsukamoto, et al., 1991; Shoff, et al., 1991). We now report that a diet providing an intake of 0.4 μmol d-γ-tocotrienol/d suppressed the growth of the B16 melanoma implanted in the flank of host mice. In our more rigorous test, a diet providing 7 μmol d-γ-tocotrienol or β-ionone/d suppressed the growth of established B16 melanomas. In vitro tests provided evidence of the additive effects of these two isoprenoids (FIG. 2A, B). The diet providing an intake of 7 μmol d-γ-tocotrienol/d increased the duration of survival by 35%. Whereas doubling the intake of d-γ-tocotrienol to 14 μmol/d did not further increase the duration of survival (−0.21 d, P=0.95), adding an intake of 7 μmol of β-ionone to that of 7 μmol d-γ-tocotrienol/d tended to increase the duration of survival (+0.83 d, P=0.65, Tables 3, 4). This study evaluated the responses of established implanted melanomas to β-ionone and d-γ-tocotrienol, two isoprenoids with structural relationships to the two antioxidant nutrients recently discounted as having tumor-suppressive actions (Greenberg and Sporn, 1996). Both isoprenoids significantly increased survival time (Table 4). We note findings that a massive intake of ascorbic acid (733 μmol/d) suppressed the growth of implanted 216 melanomas (Meadows, et al., 1991). Our studies showed that a diet providing an 8-fold elevation in d-α-tocopherol equivalents had a marginal impact on tumor growth whereas a d-γ-tocotrienol diet providing only the d-α-tocopherol-equivalent of the AIN-76A diet yielded a highly significant suppression of tumor growth.

D. Synergistic Action of Lovastatin, Tocotrienol and Ionone i. Background

Lovastatin, a fungal antibiotic, competitively inhibits 3-hydroxy-3-methylglutaryl coenzyme A (HMG CoA) reductase activity (J. L. Goldstein and M. S. Brown, *Nature* 343:425–430, 1990). β-Ionone (S.G. Yu, et al., *J. Agric. Food Chem.* 42:1493–1496, 1994) a pure isoprenoid, and related agents suppress HMG CoA reductase activity via the suppression of its synthesis (reviewed in H. Mo, et al., Nutritional Oncology, D. Huber & G. Blackburn, eds. Academic Press, N.Y., in press; C. E. Elson, et al., *Amer. Assoc. Cancer Res.*, in press). The tocotrienols, a group of mixed isoprenoids, suppress reductase activity by triggering the proteolytic degradation of the enzyme (C. E. Elson, supra, in press). As a consequence of the inhibited reductase action, lovastatin and later derivatives (J. L. Goldstein and M. S. Brown, supra, 1990; R. A. Parker, et al., *J. Biol. Chem.* 268:11230–11238, 1993), β-ionone and related pure isoprenoids (S. G. Yu, et al., supra, 1994; H. Mo, et al., supra, in press), and the tocotrienols (H. Mo, et al., supra, in press; R. A. Parker, et al., supra, 1993; A. A. Qureshi, et al., *J. Biol. Chem.* 261:10544–10550, 1986; A. A. Qureshi, et al., Proceedings of the 1996 PORIM International Palm Oil Conference, Kuala Lumpur, Malaysia, pp. 168–180, 1996) lower serum cholesterol levels. Cells treated with lovastatin have a several-fold increase in HMG CoA reductase, an increase resulting in an elevated reductase activity following the removal of the inhibitor (J. L. Goldstein and M. S. Brown, supra, 1990). Cellular activities underlying the increase in reductase mass include increases in the transcription and efficiency of processing of HMG CoA reductase mRNA and a decrease in the proteolytic degradation of the enzyme. β-Ionone (S. G. Yu, et al., supra, 1994) and the tocotrienols (R. A. Parker, et al., suira, 1993) attenuate the degree of elevation in reductase activity (S. G. Yu, et al., supra, 1994) and mass (R. A. Parker, et al., supra, 1993) effected by lovastatin treatment.

Mevalonate pathway intermediates are essential for the post-translational modification of proteins that play essential roles in cell proliferation (see H. Mo, et al., supra, in press). The competitive inhibition of mevalonate synthesis imposed by the statins suppresses the proliferation of cultured cells (J. L. Goldstein and M. S. Brown, supra, 1990) and the growth of implanted tumors (W. Maltese, et al., *J. Clin. Invest.* 76:1748–1754, 1985; J. P. Jani, et al., *Invasion Metastasis* 13:314–324, 1993). A five-year follow-up of 745 hypercholesterolemic patients receiving lovastatin, up to 80 mg/d, revealed a 33% reduction in cancer incidence (14 observed, 21 predicted) (J. A. Tolbert, *Arch. Intern. Med.* 153-1079–1087, 1993). A Phase I trial evaluated the tolerability of lovastatin administered at progressively higher doses (3 to 43 cycles of 7-day courses given monthly) involving 88 patients with solid tumors (39 with brain tumors, 24 with hormone-independent prostate cancer). Doses ranged between 2 and 45 mg/kg (the maximum dose for hypercholesterolemia is 80 mg/d). Sixty patients experienced a total of 128 episodes of toxicity; the incidence and severity of toxicity increased markedly once the 25 mg/kg dose level was reached. To prevent myotoxicity and improve the tolerability of lovastain, ubiquinone was administered to a cohort of patients receiving 30 mg/kg or higher doses of lovastatin. Ubiquinone did not decrease the incidence of musculoskeletal toxicity but significantly decreased its severity. The authors conclude with the suggestion that high-grade gliomas represent a reasonable target for Phase II trials and recommended that alternative treatment schedules aimed at achieving sustained inhibition of mevalonate synthesis be investigated (A. Thibault, et al., *Clin. Cancer Res.* 2:483–491, 1996).

ii. Ionone, Tocotrienol and Lovastatin Act Synergistically to Inhibit Tumor Cell Growth β-Ionone, γ-tocotrienol and lovastatin are known to individually suppress the proliferation of murine melanoma B16/F10 cells. $IC_{50}$ values for β-ionone and γ-tocotrienol are 140 μmol (L. He, et al., *J. Nutr.* 127:668–674, 1997), and 20 μmol/l (L. He, et al., supra). Using the protocol outlined in He, et al., supra, we have determined that B16 cells incubated with 1.9±0.3 μmol/l lovastatin grow at 61.4±4.6% the rate of controls. This value confirms the value determined using a colony formation assay (J. P. Jani, et al., supra, 1993). In vivo studies show that lovastatin (50 mg/kg) administered ip on alternate days (J. L. Goldstein and M. S. Brown, supra, 1990), β-ionone (2 mmol/kg diet) (L. He, et al., supra, 1997) and γ-tocotrienol (116–2000 μmol/kg diet) individually suppressed the growth implanted murine melanoma B16F10 tumors.

Our in vitro assays record synergy between the growth suppressive actions of the three agents. The growth-suppressive action of each combination is greater than that predicted by the sum of the individual effects (Table 5).

Table 5 tabulates the results of our in vitro assays. Table 5 lists various concentrations of lovastatin, β-ionone and γ-tocotrienol and the growth suppressive ability of each treatment. Growth in treated cells is recorded as e of control growth. On Table 5 we show that 2 μM lovastatin and 150 μM β-ionone respectively decreased cell growth by 50% and 32% (50% and 68% of control growth)—the combined action of the two compounds is predicted to suppress growth by 82% (50%±32%) or reduce cell growth to 18% of control. Growth was reduced by 90% or to 10% of control. In a series of tests combining lovastatin with an isoprene (tocotrienol or ionone) we predicted a 66% reduction in cell count (33±5% of control). However, we observed an 87% decrease (13±4% of control). Combinations of isoprenoids yielded a 50% reduction in cell growth—the predicted reduction was 57 (50% of control predicted, 43% of control obtained).

One will note that in each combination of lovastatin, β-ionone and tocotrienol, the combination resulted in less cell growth than the predicted, additive value.

Referring to Table 5, we would predict a full suppression of growth with a blend providing 2 μM lovastatin, 5 μM tocotrienol and 50 μM ionone.

APPENDIX 1—TABLES

TABLE 1

The concentrations of selected isoprenoids required to suppress the increase in the population of melanoma cells by 50% during a 48 hour incubation[1]. Also listed are representative sources and aroma characteristics of each isoprenoid.

| Isoprenoid Class | n μmol/L | $IC_{50}$ | Representative Source | Aroma |
|---|---|---|---|---|
| Monoterpenes | | | | |
| d-Limonene | 3 | 450 ± 43 | Citrus Peel, Mint | lemon |
| Perillyl alcohol | 3 | 250 ± 28 | Citrus Peel, Mint, Sage, Lavender | lilac |
| Geraniol | 3 | 150 ± 19 | Citrus Peel, Basil, Rosemary | fruit |
| Perillaldehyde | 3 | 120 ± 17 | Citrus, Basil, Rosemary | fruit |
| Carvacrol | 3 | 120 ± 15 | Thyme, Marjoram, Mint, Dill | mint |
| Thymol | 3 | 120 ± 15 | Thyme, Oregano, Tangerine Peel | thyme |
| Sesquiterpenes | | | | |
| Farnesol | 2 | 50 | Rose, Chamomile, Lavender, Lilac | lilac |
| β-Ionone | 5 | 140 ± 23 | Grapes, Corn, Apricots, Prunes | woody |
| Tocols | | | | |

TABLE 1-continued

The concentrations of selected isoprenoids required to suppress the increase in the population of melanoma cells by 50% during a 48 hour incubation[1]. Also listed are representative sources and aroma characteristics of each isoprenoid.

| Isoprenoid Class | n μmol/L | $IC_{50}$ | Representative Source | Aroma |
|---|---|---|---|---|
| d-α-Tocotrienol | 4 | 110 ± 15 | Barley, Rice, Oat Palm, Olive Oils | oily |
| d-γ-Tocotrienol | 6 | 20 ± 3 | Barley, Rice, Oat Palm, Olive Oils | oily |
| d-δ-Tocotrienol | 3 | 10 ± 3 | Barley, Rice, Oat Palm, Olive Oils | oily |
| d-2-desmethyl Tocotrienol | 3 | 0.9 ± 0.2 | Rice Bran | oily |
| dl-α-Tocopherol | 4 | >1600 | Soybean, Corn, Wheat Barley, Rice, Oats, Palm Oils | oily |

[1]Values are means ± SD.

TABLE 2

Impact of d-γ-tocotrienol on days to detection and 28-d growth of B16 melanomas implanted into the flanks of mice[1].

| Tocol | μmol/ kg diet (g) | body weight 10 d (g) | 38 d | tumor detection (d) | weight (g) | liver weight (g) |
|---|---|---|---|---|---|---|
| dl-α-Tocopherol | 116 | 17.33[a] | 23.30 | 19.55[b] | 3.59[a] | 1.18[a] |
| d-γ-Tocotrienol | 116 | 17.02[a] | 22.43 | 19.68[b] | 2.31[bc] | 1.12[ab] |
| dl-α-Tocopherol | 928 | 16.41[b] | 22.53 | 19.75[b] | 2.89[ab] | 1.06[b] |
| d-γ-Tocotrienol | 928 | 16.83[ab] | 22.56 | 22.90[a] | 1.78[c] | 1.03[b] |
| pooled SEM | | 0.10 | 0.19 | O-35 | 0.17 | 0.02 |
| | | a > b | | a > b | a > b > c | a > b |

[a–c]Means not sharing a superscript are different ($P < 0.05$).
[1]Values are means, n = 20.
[2]Days post implant for appearance of a palpable tumor.

TABLE 3

Impact of isoprenoid-enriched diets on the duration of survival of host mice bearing established melanomas[1].

| Group | d-γ-Tocotrienol mmol/kg diet | β-Ionone | Days to tumor | Days survival Mean | Median |
|---|---|---|---|---|---|
| Control | 0 | 0 | 15.00 | 13.83[b] | 15.0 |
| d-γ-Tocotrienol | 2 | 0 | 14.92 | 18.67[a] | 20.0 |
| d-γ-Tocotrienol | 4 | 0 | 14.92 | 18.46[a] | 22.0 |
| β-Ionone | 0 | 2 | 14.92 | 18.27[a] | 23.0 |
| Blend | 2 | 2 | 14.92 | 19.50[a] | 20.5 |
| pooled SEM | | | | 0.547 a > b | |

[a–b]Means not sharing a superscript are different ($P < 0.03$).
[1]Values are means, n = 12.

TABLE 4

Pairwise comparisons of isoprenoid effects on
the duration of survival following detection of a B16
melanoma in the flanks of mice.

| Group Comparison | Paired t-test | | Wilcoxon Signed Rank | |
|---|---|---|---|---|
| | t-value | P-value | Z-value | P-value |
| Control vs. | | | | |
| d-γ-Tocotrienol[1] | 5.74 | 0.01 | −2.93 | 0.01 |
| d-γ-Tocotrienol[2] | 2.70 | 0.02 | −2.22 | 0.03 |
| β-Ionone[3] | 2.81 | 0.02 | −2.18 | 0.03 |
| Blend[4] | 3.27 | 0.01 | −2.45 | 0.01 |
| d-γ-Tocotrienol[1] vs. | | | | |
| d-γ-Tocotrienol[2] | 0.46 | 0.66 | −0.47 | 0.64 |
| β-Ionone[3] | 0.06 | 0.95 | −0.15 | 0.88 |
| Blend[4] | 0.46 | 0.66 | −0.47 | 0.64 |
| d-γ-Tocotrienol[2] | | | | |
| β-Ionone[3] | 0.11 | 0.92 | −0.06 | 0.95 |
| Blend[4] | 1.36 | 0.21 | −1.42 | 0.16 |
| β-Ionone[3] vs. Blend[4] | 0.93 | 0.37 | −0.83 | 0.41 |

[1]2 mmol d-γ-tocotrienol/kg diet.
[2]4 mmol d-γ-tocotrienol/kg diet.
[3]2 mmol β-ionone/kg diet.
[4]2 mmol d-γ-tocotrienol + 2 mmol β-ionone/kg diet.

TABLE 5

| Lovastatin | β-Ionone μmol/L | γ-Tocotrienol | Growth % of Control | Predicted |
|---|---|---|---|---|
| 2 | 0 | 0 | 50 | |
| 0 | 150 | 0 | 68 | |
| 2 | 150 | 0 | 10 | 18 |
| 2 | 0 | 0 | 60 | |
| 0 | 0 | 5 | 90 | |
| 0 | 0 | 10 | 85 | |
| 2 | 0 | 5 | 32 | 50 |
| 2 | 0 | 10 | 20 | 45 |
| 1.5 | 0 | 0 | 71 | |
| 3 | 0 | 0 | 53 | |
| 0 | 0 | 10 | 72 | |
| 0 | 0 | 20 | 65 | |
| 1.5 | 0 | 10 | 20 | 43 |
| 1.5 | 0 | 20 | 10 | 36 |
| 3 | 0 | 10 | 0 | 25 |
| 3 | 0 | 20 | 0 | 18 |
| 0 | 50 | 0 | 90 | |
| 0 | 100 | 0 | 84 | |
| 0 | 0 | 7.5 | 81 | |
| 0 | 0 | 15 | 66 | |
| 0 | 50 | 7.5 | 66 | 71 |
| 0 | 100 | 7.5 | 64 | 65 |
| 0 | 50 | 15 | 51 | 56 |
| 0 | 100 | 15 | 32 | 50 |
| 0 | 150 | 0 | 32 | |
| 0 | 0 | 15 | 77 | |
| 0 | 150 | 15 | 0 | 9 |

APPENDIX 2—LITERATURE CITED

Adany, I., et al., "Differences in sensitivity to farnesol toxicity between neoplastically- and non-neoplastically-derived cells in culture," Cancer Lett. 79:175–179, 1994.

American Institute of Nutrition. Report of the American Institute of Nutrition ad hoc committee on standards for nutritional studies. J. Nutr. 107:1340–1348, 1977.

Block, G., et al., "Fruit, vegetables, and cancer prevention: A review of the epidemiological evidence," Nutr. Cancer 18:1–29, 1992.

Coni, P., et al., "Hypomethylation of β-hydroxy-β-methylglutaryl coenzyme A reductase gene and its expression during hepatocarcinogenesis in the rat," Carcinogenesis 13:497–499, 1992.

Correll, C. C., et al., "Identification of farnesol as the non-sterol derivative of mevalonic acid required for the accelerated degradation of 3-hydroxy-3-methylglutaryl coenzyme A reductase," J. Biol. Chem. 269:17390–17393, 1994.

Counts, J. L. and Goodman, J. I., "Hypomethylation of DNA: a possible epigenetic mechanism involved in tumor promotion," Prog. Clin. Biol. Res. 391:81–101, 1995.

Crane, D., "Biosynthesis of sesquiterpenes. In: Biosynthesis of Isoprenoid Compounds (Porter, J. W. and Spurgeon, S. L., eds.) vol. 1, pp. 283–374. John Wiley & Sons, New York, N.Y., 1981.

Croteau, R., "Biosynthesis of monoterpenes. In: Biosynthesis of Isoprenoid Compounds (Porter, J. W. and Spurgeon, S. L., eds.) vol. 1, pp. 225–282. John Wiley & Sons, New York, N.Y., 1981.

Crowell, P. L., et al., "Selective inhibition of isoprenylation of 21–26-kDa proteins by the anticarcinogen d-limonene and its metabolites," J. Biol. Chem. 266:17679–17685, 1991.

Cuthbert, J. A. and Lipsky, P. E., "Suppression of the proliferation of ras-transformed cells by fluoromevalonate, an inhibitor of mevalonate metabolism," Cancer Res. 55:1732–1740, 1995.

DeClue, J. E., et al., "Inhibition of cell growth by lovastatin is independent of ras function," Cancer Res. 51:712–717, 1991.

Elson, C. E., "Suppression of mevalonate pathway activities by dietary isoprenoids: Protective roles in cancer and cardiovascular disease," J. Nutr. 125:1666s–1672s, 1995.

Elson, C. E. and Qureshi, A. A., "Coupling the cholesterol- and tumor-suppressive actions of palm oil to the impact of its minor constituents on 3-hydroxy-3-methylglutaryl coenzyme A reductase activity," Prost. Leuko. Essen. Fatty Acid 52:205–208, 1995.

Elson, C. E. and Yu, S. G., "The chemoprevention of cancer by mevalonate-derived constituents of fruits and vegetables," J. Nutr. 124:607–614, 1994.

Gould, M. N., "Prevention and therapy of mammary cancer by monoterpenes," J. Cell. Biochem. S22:139–144, 1995.

Gould, M. N., et al., "A comparison of tocopherol and tocotrienol for the chemoprevention of chemically-induced mammary tumors," Am. J. Clin. Nutr. 53:1068S–1070S, 1991.

Greenberg, E. R. and Sporn, M. B., "Antioxidant vitamins, cancer and cardiovascular disease," New Engl. J. Med. 334:1189–1190, 1996.

Gruber, J. R., et al., "Increased expression of protein kinase Cα plays a key role retinoic acid-induced melanoma differentiation," J. Biol. Chem. 267:13356–13360, 1992.

Haycock, K. A., et al., "Nonparametrics. In: StatView, pp. 344–355. Abaacus Concepts, Berkeley, Calif., 1992.

Kamal-Eldin, A. and Appelqvist, L-A., "The chemistry and antioxidant properties of tocopherols and tocotrienols," Lipids 31:671–701, 1996.

Kawata, S., et al., "Increase in the active form of 3-hydroxy-3-methylglutaryl coenzyme A reductase in human hepatocellular carcinoma: Possible mechanism for alteration of cholesterol biosynthesis," Cancer Res. 50:3270–3273, 1990.

Kohl, N. E., et al., "Development of inhibitors of protein farnesylation as potential chemotherapeutic agents," J. Cell. Biochem. 22:145–150, 1995.

Komiyama, K., et al., "Studies on the biological activity of tocotrienols," *Chem. Pharm. Bull.* 37:1369–1371, 1989.

Kuwashima, Y., et al., "Responses of a murine B16 melanoma to pharmacotherapy studied and compared with different assay systems," *Cancer Res. Clin. Oncol.* 116:173–178, 1990.

Laird, P. W. and Jaenisch, R., "DNA methylation and cancer," *Human Molec. Gen.* 3:1487–1495, 1994.

Mac Neil, S., et al., "Signal transduction in murine B16 melanoma cells," *Melanoma Res.* 2:197–206, 1992.

Meadows, G. G., et al., "Ascorbate in the treatment of experimental transplanted melanoma," *Am. J. Clin. Nutr.* 54:1284s–1291s, 1991.

Meigs, T. E., et al., "Regulation of 3-hydroxy-3-methylglutaryl-coenzyme A degradation by the nonsterol mevalonate farnesol in vivo," *J. Biol. Chem.* 271:7916–7922.

Parker, R. A., et al., "Tocotrienols regulate cholesterol production in mammalian cells by post-transcriptional suppression of 3-hydroxy-3-methylglutaryl-coenzyme A reductase," *J. Biol. Chem.* 268:11230–11238, 1993.

Perez-Sala, D. and Mollinedo, F., "Inhibition of isoprenoid biosynthesis induces apoptosis in human promylocytic HL-60 cells," *Biochem. Biopys. Res. Commun.* 199:1209–1215, 1994.

Qureshi, A. A., et al., "Response of hypercholesterolemic subjects to administration of tocotrienols," *Lipids* 30:1171–1177, 1995.

Rossiello, M. R., et al., "Similar patterns of hypomethylation in the β-hydroxy-β-methylglutaryl coenzyme A reductase gene in hepatic nodules induced by different carcinogens," *Molec. Carcinogenesis* 10:237–245, 1994.

Shoff, S. M., et al., "Concentration-dependent increase in murine P388 and B16 population doubling time by the acyclic monoterpene geraniol," *Cancer Res.* 51:37–42, 1991.

Thibault, A., et al., "Phase I study of phenylacetate administration twice daily to patients with cancer," *Cancer* 75:2932–2938, 1995.

Thibault, A., et al., "Phase I studies of lovastatin, an inhibitor of the mevalonate pathway, in patients with cancer," *Clin. Cancer Res.* 2:483–491, 1996.

Tsukamoto, K., et al., "Malignant melanoma: relationship to parameters of differentiation," *Melanoma Res.* 1:223–230, 1991.

Vasudevan, S., et al., "Hypomethylation of β-hydroxy-β-methylglutaryl coenzyme A (HMG CoA) reductase gene in polyps and cancers of human colon," *FASEB J.* 8:A647, 1994 (abs.).

West, C., "Biosynthesis of diterpenes. In: Biosynthesis of Isoprenoid Compounds (Porter, J. W. and Spurgeon, S. L., eds.) vol. 1, pp. 375–411, John Wiley & Sons, New York, N.Y., 1981.

Yu, S. G., et al., "Geraniol, an inhibitor of mevalonate biosynthesis, suppresses the growth of hepatomas and melanomas transplanted to rats and mice, *J. Nutr.* 125:2763–2767, 1995.

I claim:

1. A method of inhibiting the growth of tumor cells comprising the step of exposing tumor cells to an effective amount of a composition comprising at least two compounds selected from the group consisting of tocotrienol and statin, wherein the amount is effective to inhibit tumor cell growth, wherein the inhibition is greater than the additive effects of individual compounds and wherein the tumor cells are sensitive to the composition.

2. The method of claim 1 wherein the tocotrienol is selected from the group consisting of d-γ-tocotrienol, 2-desmethyltocotrienol, d-δ-tocotrienol and d-tocotrienol.

3. The method of claim 1 wherein the tocotrienol is d-γ-tocotrienol.

4. The method of claim 1 wherein the statin is lovastatin.

5. The method of claim 1 wherein the exposing step comprises administering the composition in the form of a food.

6. The method of claim 1 wherein the exposing step comprises administering the composition in the form of a pharmaceutical.

7. The method of claim 1 wherein the composition comprises d-γ-tocotrienol and lovastatin.

8. A method of inhibiting tumor growth comprising the step of administering to a tumor patient to an effective amount of a composition comprising at least two compounds selected from the group consisting of tocotrienol and statin, wherein the amount is effective to inhibit tumor growth and wherein the tumor is sensitive to the composition and the inhibition is greater than the additive effect of the compounds.

* * * * *